(12) United States Patent
McArthur et al.

(10) Patent No.: US 11,571,493 B2
(45) Date of Patent: Feb. 7, 2023

(54) CO-PRECIPITATION METHOD

(71) Applicant: NEOMEND, INC., Irvine, CA (US)

(72) Inventors: Tina Lanette McArthur, Fallbrook, CA (US); Tracy Hutchison, New Market, AL (US); Jon McKannan, Huntsville, AL (US); Charles Vaughn Cassingham, Newport Beach, CA (US)

(73) Assignee: Neomend, Inc., Irvine, CA (US)

( * ) Notice: Subject to any disclaimer, the term of this patent is extended or adjusted under 35 U.S.C. 154(b) by 326 days.

(21) Appl. No.: 14/384,130

(22) PCT Filed: Mar. 15, 2013

(86) PCT No.: PCT/US2013/032049
§ 371 (c)(1),
(2) Date: Sep. 9, 2014

(87) PCT Pub. No.: WO2013/142322
PCT Pub. Date: Sep. 26, 2013

(65) Prior Publication Data
US 2015/0045455 A1 Feb. 12, 2015

Related U.S. Application Data

(60) Provisional application No. 61/612,943, filed on Mar. 19, 2012.

(51) Int. Cl.
| A61K 47/10 | (2017.01) |
| A61L 24/06 | (2006.01) |
| A61L 31/06 | (2006.01) |
| A61L 24/04 | (2006.01) |
| A61K 9/14 | (2006.01) |
| C08G 65/30 | (2006.01) |
| A61L 31/04 | (2006.01) |

(52) U.S. Cl.
CPC ............ A61L 24/046 (2013.01); A61K 9/146 (2013.01); A61K 47/10 (2013.01); A61L 24/043 (2013.01); A61L 24/06 (2013.01); A61L 31/041 (2013.01); A61L 31/06 (2013.01); C08G 65/30 (2013.01)

(58) Field of Classification Search
CPC ....... A61K 9/146; A61K 47/10; A61L 24/046; A61L 24/043; A61L 24/06; A61L 31/041; A61L 31/06; C08G 65/30
See application file for complete search history.

(56) References Cited

U.S. PATENT DOCUMENTS

| 5,583,114 | A | 12/1996 | Barrows et al. |
| 6,371,975 | B2 | 4/2002 | Cruise et al. |
| 6,458,147 | B1 | 10/2002 | Cruise et al. |
| RE38,158 | E | 6/2003 | Barrows et al. |
| RE38,827 | E | 10/2005 | Barrows et al. |
| 7,883,693 | B2 * | 2/2011 | Sehl ..................... C09D 167/02 424/78.03 |
| 2002/0161399 | A1 | 10/2002 | Cruise et al. |
| 2004/0156782 | A1 * | 8/2004 | Alam ................. A61K 49/0034 424/9.6 |
| 2007/0166372 | A1 | 7/2007 | Huang et al. |
| 2007/0225337 | A1 | 9/2007 | Greil et al. |
| 2010/0003337 | A1 * | 1/2010 | Hanes ................ A61K 47/6907 424/501 |
| 2010/0196280 | A1 * | 8/2010 | Fischer ................... A61P 29/00 424/9.3 |

FOREIGN PATENT DOCUMENTS

| EP | 2634179 A1 * | 9/2013 | .......... C08G 63/664 |
| WO | 2004/009672 A1 | 1/2004 | |
| WO | 2013/142322 A1 | 9/2013 | |

OTHER PUBLICATIONS

Lee et al, Journal of microencapsulation, 2006, vol. 23, No. 7, pp. 741-749.*
International Search Report and Written Opinion issued for PCT/US2013/032049 dated Jun. 28, 2013.
Martin et al., "Co-precipitation of carotenoids and bio-polymers with the supercritical anti-solvent process", *J. of Supercritical Fluids* (May 2007) 41(1):138-147.
Mattea et al., "Co-Precipitation of β-Carotene and Polyethylene Glycol with Compressed CO2 as an Antisolvent: Effect of Temperature and Concentration", *Ind. Eng. Chem. Res.* (Apr. 30, 2008) 47(11):3900-3906.
European Search Report and Written Opinion for EP13765159 dated Jun. 25, 2013.
Supplementary European Search Report and Written Opinion for EP13765159 dated Nov. 3, 2015.

* cited by examiner

*Primary Examiner* — Jared Barsky
(74) *Attorney, Agent, or Firm* — Wolf, Greenfield & Sacks, P.C.

(57) ABSTRACT

Methods for preparing a PEG composition by co-precipitation of two or more components to produce a substantially homogenous powder. According to some embodiments, the two or more components are at least and partially soluble in a solvent, and at least one component is a functionalized PEG. Contacting the at least two component with the solvent at least partially dissolves the components which are then co-precipitated. The resulting product is substantially homogenous, unlike product made by other methods. The PEG composition may be co-precipitated with additional compounds, such as a colorant like indocyanine green.

26 Claims, 3 Drawing Sheets

CO-PRECIPITATION METHOD

CROSS-REFERENCE TO RELATED APPLICATIONS

This application is a U.S. national stage filing under 35 U.S.C. § 371 of International Application No. PCT/US2013/032049 filed Mar. 15, 2013 entitled "Co-Precipitation Method," which claims benefit to and priority of U.S. Provisional Patent Application No. 61/612,943, filed on Mar. 19, 2012, entitled "Co-Precipitation Method," the entire contents of which are hereby incorporated by reference in their entireties.

GOVERNMENT INTERESTS

NOT APPLICABLE

PARTIES TO A JOINT RESEARCH AGREEMENT

NOT APPLICABLE

INCORPORATION BY REFERENCE OF MATERIAL SUBMITTED ON A COMPACT DISC

NOT APPLICABLE

BACKGROUND

This application relates to the field of blending compounds. More particularly, this application relates to methods of blending one or more polyethylene glycol (PEG) compounds with one or more other compounds. Some embodiments include a homogenous blended composition that results from such methods.

SUMMARY OF THE INVENTION

Medical adhesives, sealants and barriers are often made of hydrogel materials comprising a PEG cross-linking component. Disclosed herein are methods of preparing such PEG cross-linking components, including the PEG itself as well as possible additives.

DESCRIPTION OF DRAWINGS

The drawings submitted herewith show some embodiments or features of some embodiments encompassed by the disclosure. The drawings are meant to be illustrative and are not intended to be limiting. Like reference numeral refer to like elements through the drawings.

DETAILED DESCRIPTION

This application disclosed methods of preparing blends of polyethylene glycol (PEG). Such blends are useful in many processes and end uses, but are particularly contemplated for use in a two-part medical adhesive, sealant or barrier such as, but not limited to, those disclosed and described in U.S. Pat. Nos. 5,583,114; RE38,158; RE38,827; 6,371,975; 6,458,147, each of which is hereby incorporated by reference in its entirety.

Such a medical adhesive comprises a protein, such as, but not limited to albumin or albumin fragments, and a cross-linker, where the cross-linker is PEG based. This application is concerned mainly with the PEG based cross-linker composition. Reference herein to "medical adhesive" is meant to be inclusive of medical adhesives, sealants, and barrier compositions, particularly hydrogel based compositions.

The PEG composition can be prepared through the blending processes described herein. The blending process allows for additional molecules or compounds of interest to be incorporated into the blend. These molecules have a number of benefits, including but not limited to varying degradation rate, release rate, visual aid, therapeutic drug and/or protein delivery, addition of distingrants and/or dispersants to provide accelerated and/or consistent dissolution times, potential pegylated molecules for drug delivery, and incorporation of microencapsulated and/or nanoparticles, nanocages/nanoshell to deliver drugs, heat, light or other substances to specific types of cells, additional advantages and uses will also be apparent.

A medical adhesive must be absorbed or broken down in vivo, without producing an allergic response, adverse tissue reaction or systemic toxic effects, in an acceptable time period. Preferably, a suitable adhesive would also be readily absorbed after it is applied.

Many key properties of some existing PEG based medical adhesives, sealants and barriers are maintained and in some cases may be improved by using PEG blended according to the methods described herein. The following are examples of a few of various sealant properties prepared using some of the methods disclosed herein. Some or all of these properties are desirable in a final medical adhesive:

Sealant burst pressures range from, but are not limited to, about 90 mmHg to about 300 mmHg. In some embodiments, burst pressure may also be about 40 mm Hg or lower depending on the intended use, e.g. different body regions may require more or less burst strength.

Elastic modulus between, but not inclusive of, 3 kPa to 100 kPa.

Degradation from about 3 days out to more than about 90 days.

Swelling, though not limited to, less than 1% to >200% and may in some cases contract. In some cases, swelling is about 0.1%, about 0.5%, about 0.7%, about 0.9%, about 1%, about 3%, about 5%, about 7%, about 10%, about 20%, about 30%, about 40%, about 50%, about 60%, about 70% about 80%, about 90%, about 100%, about 125%, about 150%, about 175%, about 200%, or ranges between any two of these.

During hydrolysis of the sealant, the hydrogel breaks down into the various components from which the cross-linker was synthesized, and the albumin is released, The cross-linker components may include, but are not limited to, the starting raw PEG polymer, succinic acid, lactic acid, glutaric acid and n-hydroxy succinic acid, and or other degradation products from the various functionalized PEGs used in the co-precipitate blending process or high shear granulation process or top spray process.

The adhesive and sealant composition of this invention may be used in a variety of applications. Some applications include using the adhesive sealant composition to seal or bind tissue together either as an adjunct to or as a replacement of sutures, staples, tapes and/or bandages. In addition these compositions, in some cases, can also act as an adhesive barrier.

Medical adhesives comprising cross-linked proteins are known; however, unique and different methods of preparing the cross-linker component, and their use in such medical adhesives have not been disclosed.

This application discloses processes for blending one or more polyethylene glycol composition, and/or one or more additional molecules or compounds of interest. In some embodiments, a co-precipitation method is used. In other embodiments, compounding methods are employed. In some embodiments, the one or more polyethylene glycol composition may be a functionalized PEG. In either method, at least one PEG compound is blended with an additional compound or molecule.

The one or more polyethylene glycol compound can be any suitable PEG composition, whether linear or branched. In some embodiments, the one or more PEG composition is functionalized and may be monofunctional, bi-functional, tri-functional, or having a functionality greater than three (i.e. n>3), or a blend thereof. The PEG composition may be substantially pure or blended with other PEG compositions. The PEG composition may have a molecular weight from 1,000 Dalton/mol to 60,000 Dalton/mol.

The one or more additional molecules or compounds can be any molecule or compound that contributes to a desirable property or to provide a deliverable. Suitable additional molecules or compounds include but are not limited to: additional cross-linking compounds, a functionalized PEG, an unfunctionalized PEG, poly(ethylene glycol), poly(ethylene oxide), poly(vinyl alcohol), poly(vinylpyrrolidinone), poly(ethyloxazoline), and poly(ethylene glycol)-co-poly (propylene glycol) block copolymers, BHT or other radiation sterilization stabilizers, pharmaceuticals, statins, bioactive agents, antibiotics, peptide(s), therapeutic drug(s) or protein(s), microencapsulated molecules/drugs, nanoparticles, nanocages/nanoshells, colorants, disintegrants, dispersants, visual aids, radiological markers, fibrins, thrombins, radiopacifiers, silver, chemotherapy agents, growth factors, excipients, other molecular weight PEGs, or combinations thereof. In some embodiments, the additional molecule or compound is pegylated. In some embodiment, the additional molecule or compound is not pegylated.

In many cases, a visual aid or colorant is desirable, to distinguish one reactant from another, and to visualize the adhesive or final composition in situ. For example, sealants routinely use the FD&C family color additives. These dyes are often added to the cross-linker polyethylene glycol (PEG) powder component as a separate powder. Although any suitable colorant or visual aid may be used, the incorporation of Indocyanine Green (IcG) into a PEG blend is particularly contemplated here.

Co-Precipitation Methods

Various mixtures/blends may be created through a co-precipitation blending process. In some embodiments, the additional molecules are co-precipitated with the one or more functionalized polyethylene glycol cross-linker. In other embodiments, one or more additional molecules can be pegylated prior to the co-precipitation. The one or more additional molecules or compounds include, but are not limited to biocompatible molecules, colorants, therapeutic drugs/proteins, antibiotics, nanoparticles and/or dispersants and disintegrates.

Applicants have developed a process for blending one or more PEG cross-linker(s) in a solvent, either with or without an additional molecule(s), by first dissolving the PEG cross-linker and any additional molecule or compound, followed by precipitating the blended solution as a homogenous powder. This process is referred to as "PEG co-precipitation" (Co-ppt). This co-precipitation process yields homogeneous particles by design of variable material composition throughout the final powder product making the physical characteristics of the final product in which it is used (e.g. the bioadhesive) more uniform. The PEG powder itself has some or all of the following advantages as well: increased homogeneity, increased flowability, easier dissolution, reduced settling, etc.

The co-precipitation process uses a solvent where all molecules are either completely soluble or possibly only partially soluble. These solvents include, but are not limited to methanol, 2-propanol, ethanol, methyl tert-butyl ether, ethyl ether, dichloromethane, methanol, dimethyl sulfoxide (DMSO), acetonitrile, and combinations thereof. One or more of the components, i.e. either the PEG or the additional molecule or compound, may be brought up in a different solvent prior to mixing with the other components. For example, and in particular, Indocyanine Green (IcG) may first be dissolved in DMSO or Methanol, and then added to a PEG solution.

The PEG solution includes PEG molecules with molecular weights between 1,000 Dalton/mol to 60,000 Dalton/mol. The PEG molecules can be in the form of monofunctional, Bi-functional, hetero-bifunctional branched and multi-functional moieties. Non-functionalize PEG(s) may also be present of similar molecular weight(s).

The functionalized sites may include electrophiles, nucleophiles or other reactive entities. They may be present in any ratio, and/or blend of active sites. Such electrophiles may include, but are not limited to, butyraldehyde, propionaldehyde, epoxide, succinimidyl carbonate or Nitrophenyl Carbonate. Nucleophiles may include, but are not limited to, succinimidyl Carboxymethyl, Succinimidyl Glutarate, Succinimidyl Succinate, or Succinimidyl Valerate. Other reactives sites may include, but are not limited to, amines, amides, sulfhydryl, maleimide, orthopyridyl disulfide, thiol, and vinyl such as an acrylate. In some embodiments, the rate of degradation may be controlled by the selection of chemical moiety in a degradation control region DCG of the PEG compound. If degradation is desired, a hydrolytically or enzymatically degradable moiety can be selected. Examples of hydrolytically degradable moieties include saturated di-acids, unsaturated di-acids, poly(glycolic acid), poly(DL-lactic acid), poly(L-lactic acid), poly(ε-caprolactone), poly(δ-valerolactone), poly(γ-butyrolactone), poly(amino acids), poly(anhydrides), poly(orthoesters), poly(orthocarbonates), and poly(phosphoesters). In some embodiments, the electrophile may further comprise an acid derivative, such as a derivative of lactic acid. Some exemplary PEGs include PEG di(succinimidyl succinimide), PEG tetra(succinimidyl glutarate)-dilactide, etc.

Bioactive agents, antibiotics, statins, peptide(s), therapeutic drug(s), protein(s), and/or nanoparticles, nanocages/nanoshells may be introduced either through/in the co-precipitation process or pegylated onto one or more arms of a PEG used in the co-precipitation process.

Alternatively, disintegrates or dispersants may also be pegylated and/or introduced into the co-precipitation. Any or all of these substances added to the PEG blends may be included in the amorphous structure of the functionalized PEGs as the PEGs crystallize. In addition, deposits of these molecules on the external portion of the functionalized PEG may occur during the PEG co-precipitation drying steps.

Co-precipitation can occur through various conditions, for example, a change in temperature, or addition of the mix to another solvent, such as Ethyl Ether or 2-Propanol, for precipitating. The co-ppt can be done with or without the biocompatible dye, for the blending of multiple PEGs. In some examples, reducing temperature will initiate co-precipitation. For example, a precipitation flask can be kept in an ice/NaCl bath to maintain 4 to 5° C. until co-precipitation is complete, and/or the temperature/temperature ramp can be controlled through a thermal jacketed mixing container.

Additional steps such as sterile filtration, additional dissolution steps, distillation, evaporation, alternative solvent exchange methods, drying, and other steps may be used during the process. The co-precipitation process yields a substantially homogenous product that also aids with secondary processing. For example, it is believed that due to the homogenous nature of the powder and its uniform particle size, that in addition to improved flow quality, the powder also aids in tablet formation, lyophilization, and many other processes. The homogeneity and uniform particle size is also believed to reduce settling. Reduced dissolution time or effort has also been seen, compared to traditional formulations.

Some benefits of the co-precipitated material includes a homogenous powder, yields low variability lot to lot, provides consistent PEG properties and additional component concentration within lot, minimal to no effect on functionality of starting PEG cross-linker(s), no effect on sealant properties such as burst, gelation kinetics, degradation, peg functionality, etc.; and desired particle size is achieved with potential to improve ease of handling and fill processing.

Some embodiments include a method of preparing a PEG composition, the method comprising: providing a solvent; providing at least two components that are at least partially soluble in the solvent; wherein at least one of the at least two components is a functionalized PEG; contacting each of the at least two components together with the solvent to at least partially dissolve each of the at least two components in the solvent; and co-precipitating each of the at least two components to yield a substantially homogenous powder.

In some embodiments, the dissolution of the various components in the various solvents may be facilitated by the addition of heat, mixing, or both.

In some embodiments, evaporation and/or distillation of various solvents may facilitate the blending, and/or exchange of solvents.

In some embodiments, the at least two components are selected from functionalized PEG, unfunctionalized PEG of similar MW, poly(ethylene glycol), poly(ethylene oxide), poly(vinyl alcohol), poly(vinylpyrrolidinone), poly(ethyloxazoline), and poly(ethylene glycol)-co-poly(propylene glycol) block copolymers, BHT or other radiation sterilization stabilizers, pharmaceuticals, statins, bioactive agents, antibiotics, statins, peptide(s), therapeutic drug(s) or protein(s), and/or nanoparticles, nanocages/nanoshells, colorants, disintegrates or dispersants, visual aids, therapeutic drugs and proteins, disintegrates and/or dispersants, radiological markers, fibrins, thrombins, radiopacifiers, silver, antibiotics, chemo agents, growth factors, excipients, disintegrants and other molecular weight PEGs, or pegylated versions thereof.

In some embodiments, at least one of the at least two components is a colorant. In some embodiments, the colorant is a pigment, dye, or visual aid. In some embodiments, the colorant is IcG.

In some embodiments, the functionalized PEG comprises a PEG having one or more electrophilic group, nucleophilic group, a reactive entity, or a combination thereof.

In some embodiments, the functionalized PEG may be linear, branched, and have a functionality where n is the number of functional groups and n is 1, n is 2, n is 3 or n can be greater than 3, or the PEG can be a blend thereof.

In some embodiments, one or more of the at least one components is at least partially dissolved in a precursor solvent prior to contacting with the solvent.

The precursor solvent is independently selected from, but not limited to, methanol, 2-propanol, ethanol, methyl tert-butyl ether, dichloromethane, dimethyl sulfoxide (DMSO), and combinations thereof.

In some embodiments, the solvent is an organic solvent. In some instances, the solvent is selected from methanol, 2-propanol, ethanol, methyl tert-butyl ether, dichloromethane, dimethyl sulfoxide (DMSO), and combinations thereof.

The co-precipitation step may be initiated in any suitable manner. In some instances, the co-precipitating step is initiated by any of a change in temperature, addition of another solvent (e.g. ethyl ether or 2-propanol).

In some embodiments, a solvent exchange can be used. In some embodiments, additional filtration and/or sterilization steps may be employed.

EXAMPLES

Figure 1:
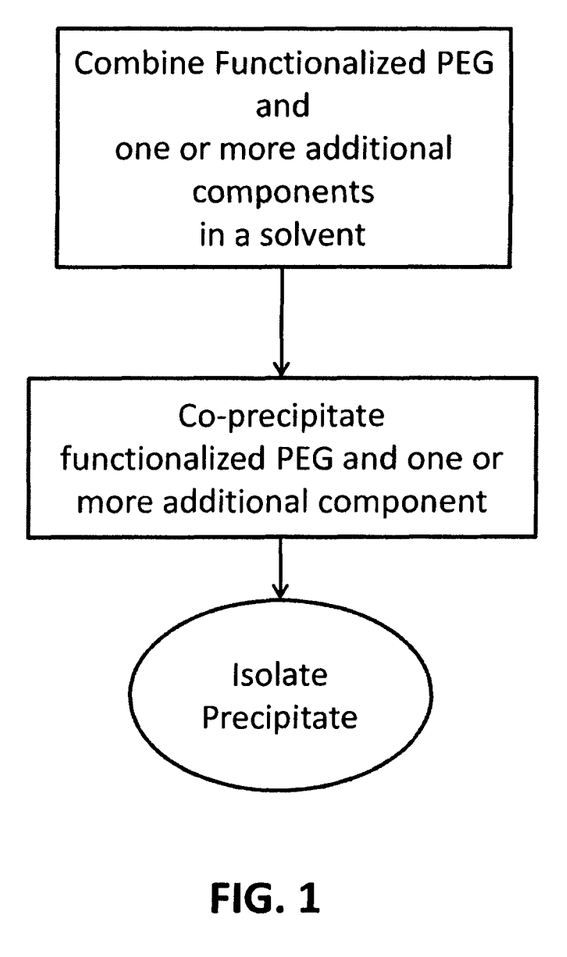
FIG. 1 is a flowchart of one exemplary method according to the disclosure herein.

FIG. 1 shows a flowchart for one exemplary reaction blending a functionalized PEG with IcG, using a precursor solvent to ensure dissolution.

The following procedures were proposed for 5 small scale co-precipitations using different methodology, solvents and nonsolvents.

Upon dissolution of the components, a small amount of solution will be removed and dried to a solid for NMR analysis to use as a reference for component ratio of the final precipitate.

Procedure

I. Recrystallization from 2-Propanol, 5 g
 1. Weigh 4.16 g 4 arm PEG-DL-SG10K (PEG tetrasuccinimidyl glutarate dilactide) and add that to a 250 m I round bottom flask;
 2. Weigh 0.84 g SS-PEG-SS 3400 and add that to the same 250 ml flask;
 3. Add 100 ml 2-Propanol and 0.0002 g of BHT and seal the flask with a stopper;
 4. Place the solution in a bath and heat with mixing until all the solids are dissolved;
 5. Remove 5 ml of solution and place that in a test tube and dry under vacuum (this sample is for NMR analysis for the component ratio standard);
 6. Remove the flask from the bath and place the round bottom flask on a stir plate;
 7. Mix the solution at room temp for 2 hours;
 8. Place the flask in an ice bath and mix the solution for an additional 1 hour;
 9. Filter the precipitate under argon gas;
 10. Dry the precipitate under vacuum for the night;
 11. Transfer the remaining dry powder to a 60 ml amber glass bottle and manually break up the clumps with a spatula;
 12. Backfill the bottle with argon gas and place the lid on tightly.

II. Recrystallization from Ethanol and MtBE, 5 g
1. Weigh 4.16 g 4 arm PEG-DL-SG10K and place into a 250 m l round bottom flask;
2. Weigh 0.84 g of SS-PEG-SS 3400 and add that to the same 250 m I flask;
3. Add 45 ml of ethanol 95 ml MtBE and 0.002 g of BHT and seal the flask with a stopper;
4. Place the solution in a bath and heat with mixing until all the solids are dissolved;
5. Remove 7 ml of solution and place that in a test tube and dry under vacuum (this sample is for NMR analysis for the component ratio standard);
6. Remove the flask from the bath and place the round bottom flask on a stir plate;
7. Mix the solution at room temp for 2 hours;
8. Place the flask in an ice bath and mix the solution for an additional 1 hour;
9. Filter the precipitate under argon gas;
10. Dry the precipitate under vacuum for the night;
11. Transfer the remaining dry powder to a 60 ml amber glass bottle and manually break up the clumps with a spatula;
12. Backfill the bottle with argon gas and place the lid on tightly.

III. Precipitation from Dichloromethane into Ethyl Ether, 5 g
1. Weigh 4.16 g 4 arm PEG-DL-SG 10K and place into a 100 ml round bottom flask;
2. Weigh 0.84 g of SS-PEG-SS 3400 and add that to the same 250 ml flask;
3. Add 5 ml of Dichloromethane and seal the flask with a stopper;
4. Mix the solution until all the solids are dissolved;
5. Remove 0.2 ml of solution and place that in a test tube and dry under vacuum (this sample is for NMR analysis for the component ratio standard);
6. Add 100 ml of Ethyl Ether to a 500 ml flask with a stir bar;
7. Add 0.002 g of BHT to the Ethyl Ether and mix until dissolved;
8. Add the PEG solution to the mixing ether slowly with vigorous mixing;
9. Mix the precipitation for 15 minutes at room temp;
10. Filter the precipitate under argon gas;
11. Dry the precipitate under vacuum for the night;
12. Transfer the remaining dry powder to a 60 ml amber glass bottle and manually break up the clumps with a spatula;
13. Backfill the bottle with argon gas and place the lid on tightly.

IV. Precipitation from Dichloromethane into 2-Propanol, 5 g
1. Weigh 4.16 g 4 arm PEG-diSG 10K and place into a 100 ml round bottom flask;
2. Weigh 0.84 g of SS-PEG-SS 3400 and add that to the same 250 m I flask;
3. Add 5 ml of Dichloromethane and seal the flask with a stopper;
4. Mix the solution until all the solids are dissolved;
5. Remove 0.2 ml of solution and place that in a test tube and dry under vacuum (this sample is for NMR analysis for the component ratio standard);
6. Add 125 ml of 2-Propanol to a 500 ml flask with a stir bar;
7. Add 0.002 g of BHT to the 2-Propanol and mix until dissolved;
8. Add the PEG solution to the mixing ether slowly with vigorous mixing;
9. Mix the precipitation for 30 minutes at room temp;
10. Filter the precipitate under argon gas;
11. Dry the precipitate under vacuum for the night;
12. Transfer the remaining dry powder to a 60 ml amber glass bottle and manually break up the clumps with a spatula;
13. Backfill the bottle with argon gas and place the lid on tightly.

V. Evaporation of Dichloromethane to a Solid, 5 g
1. Weigh 4.16 g 4 arm PEG-DL-SG10K and place into a 100 ml round bottom flask;
2. Weigh 0.84 g of SS-PEG-SS 3400 and add that to the same 250 ml flask;
3. Add 25 ml of Dichloromethane and 0.0001 g of BHT and seal the flask with a stopper;
4. Mix the solution until all the solids are dissolved;
5. Place the flask on a rotary evaporator and evaporate the solvent at 40° C. until a solid is obtained;
6. Place a vacuum adapter on the flask and attach it to a vacuum pump;
7. Dry the product under vacuum for the night;
8. Remove the flask from the vacuum source and break up the solids with a spatula;
9. Transfer the remaining dry powder to a 60 ml amber glass bottle;
10. Backfill the bottle with argon gas and place the lid on tightly.

Example 1(I) through 1(V): PEG(SS)$_2$ and PEG(SG)$_4$ dilactide, no biocompatible dye (five co-precipitation methods were used successfully) were prepared via methods similar to those disclosed above.

I. Recrystallization from 2-Propanol

| Reagent | Lot | Amount (g) | MW | mMoles |
|---|---|---|---|---|
| 4Arm-PEG-dl-SG 10K | M106597 | 4.1606 | 10000 | 0.41606 |
| SS-PEG-SS 3400 | 019K7275 | 0.8402 | 3400 | 0.2471 |
| BHT | | 0.0024 | 220.35 | 0.0109 |
| 2-Propanol | | 100 mL | 60.10 | 1306.16 |

Experimental: The 4Arm-PEG-dl-SG 10K and SS-PEG-SS 3400 were added to a 250 mL round bottom flask containing a magnetic stir bar under an argon atmosphere. To this was added BHT followed by 2-Propanol. The mixture was heated under Argon until all of the solids were dissolved. The temperature was monitored vs. time throughout the heating and cooling process. The reaction mixture was removed from the heat and a 5 mL sample was removed, labeled as the component ratio standard and dried under high vacuum. The remaining solution was stirred at ambient temperature for 2 hours followed by cooling in an ice/salt water bath for 1 hour. The product was collected by filtration under argon and dried overnight under high vacuum. Yield: 3.6 g II. Recrystallization from Ethanol and Methyl tert-Butyl Ether

| Reagent | Lot | Amount (g) | MW | mMoles |
|---|---|---|---|---|
| 4Arm-PEG-dl-SG 10K | M106597 | 4.1608 | 10000 | 0.41608 |
| SS-PEG-SS 3400 | 019K7275 | 0.8403 | 3400 | 0.2471 |
| BHT | | 0.0031 | 220.35 | 0.0141 |
| Ethanol | | 45 mL | 46.07 | 770.68 |
| Methyl tert-Butyl Ether | | 95 mL | 88.15 | 797.50 |

Experimental: The 4Arm-PEG-dl-SG 10K and SS-PEG-SS 3400 were added to a 250 mL round bottom flask containing a magnetic stir bar under an argon atmosphere. To this was added BHT followed by ethanol and methyl tert-butyl ether. The mixture was heated under Argon until all of the solids were dissolved. The temperature was monitored vs. time throughout the heating and cooling process. The reaction mixture was removed from the heat and a 5 mL sample was removed, labeled as the component ratio standard and dried under high vacuum. The remaining solution was stirred at ambient temperature for 2 hours followed by cooling in an ice/salt water bath for 1 hour. The product was collected by filtration under argon and dried overnight under high vacuum. Yield: 4.1 g III. Precipitation from Dichloromethane into Ethyl Ether

| Reagent | Lot | Amount (g) | MW | mMoles |
| --- | --- | --- | --- | --- |
| 4Arm-PEG-dl-SG 10K | M106597 | 4.161 | 10000 | 0.4161 |
| SS-PEG-SS 3400 | 019K7275 | 0.842 | 3400 | 0.2476 |
| BHT | | 0.002 | 220.35 | 0.0091 |
| Dichloromethane | | 5 mL | 84.93 | 78.01 |
| Ethyl Ether | | 100 mL | 74.12 | 952.51 |

Experimental: The 4Arm-PEG-dl-SG 10K and SS-PEG-SS 3400 were added to a 100 mL round bottom flask containing a magnetic stir bar under an argon atmosphere. To this was added Dichloromethane via a syringe with stirring until all reagents were dissolved. A 0.2 mL sample was removed, labeled as the component ratio standard and dried under high vacuum. The remaining reaction mixture was poured into a 500 mL round bottom flask containing ethyl ether, BHT and a magnetic stir bar with vigorous stirring for 15 minutes under argon. The product was collected by filtration under argon and dried overnight under high vacuum. Yield: 3.8 grams IV. Precipitation from Dichloromethane into 2-Propanol

| Reagent | Lot | Amount (g) | MW | mMoles |
| --- | --- | --- | --- | --- |
| 4Arm-PEG-dl-SG 10K | M106597 | 4.1607 | 10000 | 0.41607 |
| SS-PEG-SS 3400 | 019K7275 | 0.8415 | 3400 | 0.2475 |
| Dichloromethane | | 5 mL | 84.93 | 78.01 |
| BHT | | 0.0021 | 220.35 | 0.0095 |
| 2-Propanol | | 125 mL | 60.10 | 1632.70 |

Experimental: The 4Arm-PEG-dl-SG 10K and SS-PEG-SS 3400 were added to a 100 mL round bottom flask containing a magnetic stir bar under an argon atmosphere. To this was added Dichloromethane via a syringe with stirring until all reagents were dissolved. A 0.2 mL sample was removed, labeled as the component ratio standard and dried under high vacuum. The remaining reaction mixture was poured into a 500 mL round bottom flask containing 2-Propanol, BHT and a magnetic stir bar with vigorous stirring for 30 minutes under argon. The product was collected by filtration under argon and dried overnight under high vacuum. Yield: 3.2 grams V. Evaporation of Dichloromethane to a Solid

| Reagent | Lot | Amount (g) | MW | mMoles |
| --- | --- | --- | --- | --- |
| 4Arm-PEG-dl-SG 10K | M106597 | 4.163 | 10000 | 0.4163 |
| SS-PEG-SS 3400 | 019K7275 | 0.841 | 3400 | 0.2474 |
| Dichloromethane | | 25 mL | 84.93 | 390.03 |
| BHT | | 0.0017 | 220.35 | 0.0077 |

Experimental: The 4Arm-PEG-dl-SG MK and SS-PEG-SS 3400 were added to a 250 mL round bottom flask containing a magnetic stir bar under an argon atmosphere. To this was added BHT followed by Dichloromethane via a syringe with stirring until all reagents were dissolved. The mixture was concentrated in vacuo and dried under high vacuum. Yield: 3.7 g For reference, the initial 4Arm-PEG-dl-SG 10K and SS-PEG-SS 3400 were tested by NMR. The purity of the starting materials by NMR is listed below:

| | |
| --- | --- |
| 4Arm-•PEG-dl-SG 10K | 97.5% |
| SS-PEG-SS 3400 | 98.9% |

From these results, one of the 4Arm-PEG-dl-SG 10K methylene groups at 1.9 ppm was set at 780 and used as the reference peak by NMR. For SS-PEG-SS 3400, the methylene group at 2.9 ppm will be integrated to determine the ratio of 4Arm-PEG-dl-SG 10K/SS-PEG-SS 3400. Based on the amount of 4Arm-PEG-dl-SG 10K and SS-PEG-SS 3400 used in each experiment, the table below shows the calculated values for each methylene by NMR.

| Expt# | Lot# | 4ArmPEG-Cfl SG 10K used | SS-Peg-SS 3400 used | 4ArmPEG-dlSGlOK moles | SS-PEG SS 3400 moles | ratio 4arm/ss | 4ArmPEGdl-SG10K expected | SS-Peg-SS 3400 expected |
| --- | --- | --- | --- | --- | --- | --- | --- | --- |
| 1 | 124-5 | 4.161 | 0.84 | 0.000416 | 0.000247 | 1.684214 | 780 | 234.88 |
| 2 | 124-6 | 4.161 | 0.84 | 0.000416 | 0.000247 | 1.684214 | 780 | 234.88 |
| 3 | 124-2 | 4.161 | 0.842 | 0.000416 | 0.000248 | 1.684214 | 780 | 235.44 |
| 4 | 124-4 | 4.161 | 0.842 | 0.00041G | 0.00024S | 1.684214 | 7S0 | 235.44 |
| 5 | 124-1 | 4.163 | 0.841 | 0.000416 | 0.000247 | 1.68302 | 780 | 235.05 |

The actual values obtained by NMR are shown in the table below:

| Experiment # | Lot # | 4ArmPEGdl-SG 10K actual | SS-Peg-SS 3400 actual |
|---|---|---|---|
| 1 | 124-5 | 779.00 | 268.89 |
|   | 124-5 sample | 779.00 | 226.17 |
| 2 | 124-6 | 779.00 | 276.96 |
|   | 124-6 sample | 779.00 | 244.58 |
| 3 | 124-2 | 779.00 | 287.69 |
|   | 124-2 sample | 779.00 | 286.25 |
| 4 | 124-4 | 779.00 | 275.36 |
|   | 124-4 Sample | 779.00 | 283.70 |
| 5 | 124-1 | 779.00 | 270.35 |

Figure 2:
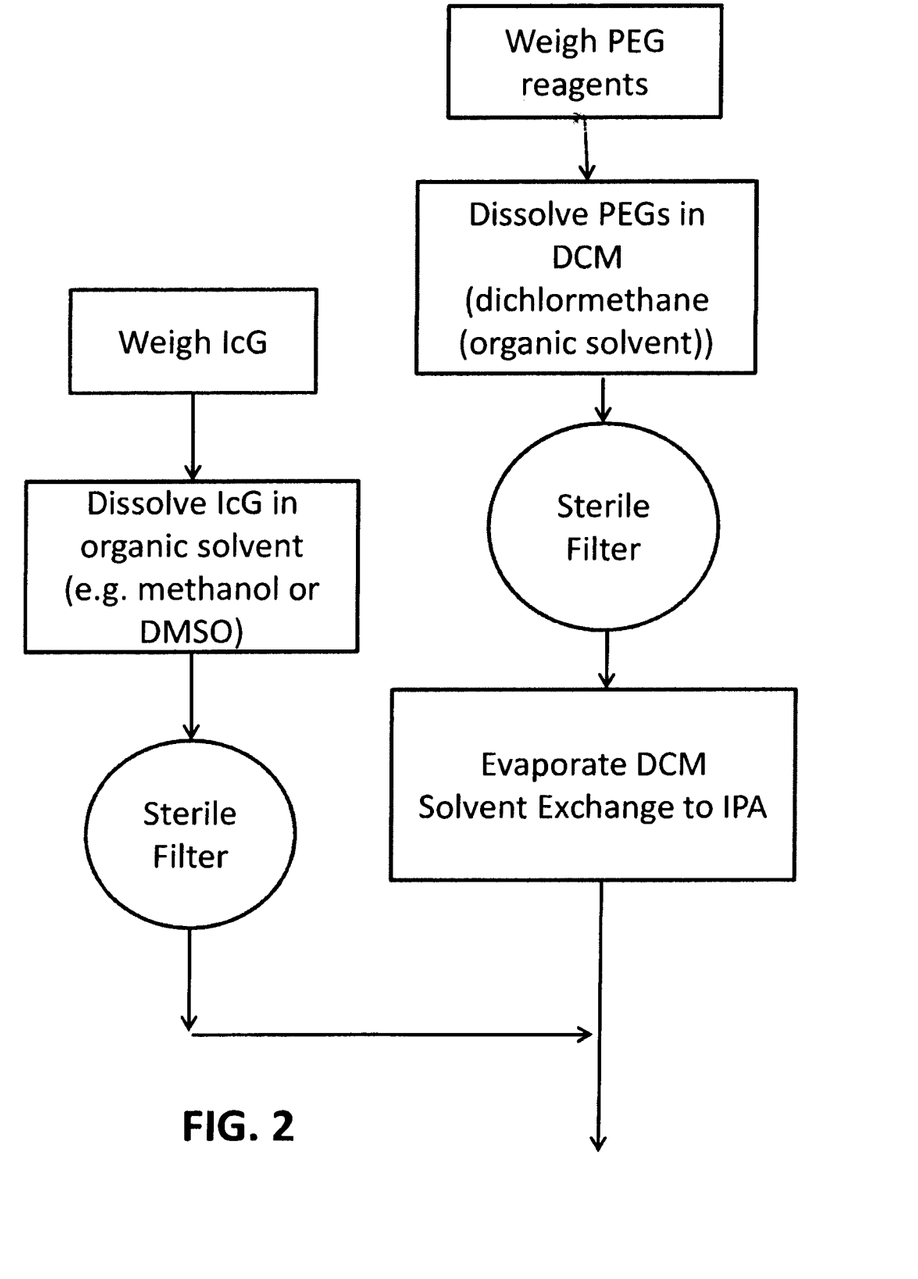
FIG. 2 is a flowchart of one exemplary method for producing a PEG composition with Indocyanine Green, IcG, colorant in accordance with some embodiments disclosed herein.

Several other blends were prepared using methods similar to that set out in FIG. 2, which involve dissolving a colorant (IcG) in a precursor solvent.

Example 2

PEG(SS)$_2$ and PEG(SG)$_4$ Dilactide with IcG

PEG(SS)$_2$ and PEG(SG)$_4$ dilactide and IcG were co-precipitated from a single solution to yield a homogenous green powder. Crystallization form on IPA

| 4 Arm-PEG SG4-2LA-10K | 4.166 g |
|---|---|
| SS-PEG-SS 3400 | 0.8411 g |
| BHT | 0.0003 g |
| ICG | 15 mg |
| IPA | 100 ml |

The material was combined with IPA and stirred at 50° C. The material was filtered and cooled in a dry ice bath. The product was collected by filtration and dried. yield: 38 g.

Example 3

PEG(SS)$_2$ and PEG(SG)$_4$ with IcG

PEG(SS)2 and PEG(SG)4 and IcG were co-precipitated from a single solution to yield a homogenous green powder. A DSI mixture (DSI 49.9 g) was added to a 2 L beaker (007001). To this was added DCM (1000 ml, Lot 0002) and stirred until dissolved. The mixture was filtered through a glan filter apparatus (0.1 um filter) into a 2 L vacuum flash (021001). The filtrate was added to a 3 L RB flask (042001) and concentrated on RVP-01, bath temp. 40° C. to a very thick oil. To this was added under argon BHT (0.0085) and IPA (1000 ml, 0042). This mixture was heated at 60° C. until all solid dissolved. To this was added via syringe and 0.2 um filter ICG (579 mg in DMSO). This mixture was stirred at 60° C. for 5 minutes to mix after the 5 minutes, the mixture was poured into a 4 L Erlenmeyer flask (022001) and stirred for 60 minutes in an ice/salt/water bath. The mixture was filtered under Argon. Product was transferred and dried. Yield: 47.8 g.

Example 4

PEG(SS)$_2$ with IcG

PEG(SS)$_2$ and IcG were co-precipitated from a single solution to yield a homogenous green powder.

| Reagent | Lot | Amount |
|---|---|---|
| SS-PEG-SS 3400 | 113-58 | 35 g |
| IPA |  | 700 ml |
| ICG |  | 0.27 g |
| DMSS |  | 14 ml |

The SS-PEG-SS 3400 was taken up inn IPA at 60° C. no solids were noticed, the solution of ICG in DMSO was added via a syringe through a 0.2 um filter. The mixture was heated to 60° C. and allowed to cool and then chilled on an ice/salt/water bath. The solid was collected by filtration and dried. Yield: 34.1 g. ICG=2000 ppm A test protocol demonstrating the usefulness of the co-precipitated material as compared to hand-blended materials, particularly in the medical adhesive/sealant/barrier context is reproduced below.

It should be understood that these and other blends can be made with these and similar methods as described and disclosed herein. Through the methods disclosed, any of a wide variety of PEG and other materials can be blended into a substantially homogenous powder which is well-suited for a variety of uses.

Compounding Techniques for PEG(s)

High Shear Granulation and Milling

A compounding technique, High Shear Granulation with Milling, is also contemplated herein. The bowl temperature is elevated slightly and controlled to the point where the PEG(s) is at the verge of melting, and becomes very "sticky" and starts to granulate. Accordingly, the method may be substantially solvent-free. Large particles are produced and then milled to the desired final particle size. A fairly tight size distribution is achieved. This technique is useful in granulating PEG(s), e.g. functionalized PEG, with or without additives, e.g. a color IcG, and proved to work well in powder filling operations.

Shear and an increase in temperature during this method are of concern. Both of these parameters negatively effect, to some degree, the PEG functionality and consequently gelation kinetics in an adhesive product. This may result in a shorter ambient shelf life for the PEG(s) powder. However, these parameters may be mitigated with further optimization.

Top Spray Fluid Bed Method

An alternative technique uses a Top Spray Fluid Bed. A solvent is required to bind the material. The material (PEG either with or without additional components) can be completely or slightly soluble in the solvent. A common solvent used in this technique is Ethanol; an alternative, though not limited to, solvent might be 2-Propanol. No heat, shear, grinding or moisture is involved in this process. Particles are agglomerated directly to the desired particle size.

In some embodiments, the method begins with a very small particle on the order of ≤80 micron. In this method, the blend is built up to the desired particle size, creating particles sizes 10× from the starting particle size. In some embodiments, the particle size may be increased about 5×, about 10×, about 15× or ranges between any two of these. Particle size may be limited due to the orifice size of cartridges. In some embodiments, this orifice size limited in the final particle size to <1000 micron. The density of the particle size can be maintained to ensure accurate fill mass for cartridges. Current synthesis of PEG(s) creates particles of varying sizes, though ideally <2000 microns. This method provides the potential to manufacture functionalized PEG(s) powder at a different particle size, creates desired particle size for ease of handling and fill processing, has bulk consistency in lot to lot. There may be slight variation from lot to lot with respect to IcG concentration and possibly slight decrease in compounded PEG(s) functionality.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "comprises" should be interpreted as "includes but is not limited to," etc.)

It should also be understood, that although various compounds, compositions, methods, and devices are described in "open" terms of "comprising," "including," or "having" various components or steps (interpreted as meaning "including, but not limited to"), the compounds, compositions, methods, and devices can also "consist essentially of" or "consist of" the various components and steps, and such terminology should be interpreted as defining essentially closed-member groups. This paragraph is not meant in any way to limit the meaning of "comprising", "having," or "including" (and other verb forms thereof), which are to be interpreted as open-ended phrases meaning "including but not limited to" consistent with patent law and custom. The intent of this paragraph is merely to indicate that the closed-member groups defined by the "consisting of" or "consisting essentially of" language are lesser included groups within the open-ended descriptions and to provide support for claims employing the "consisting of" or "consisting essentially of" language.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 substituents refers to groups having 1, 2, or 3 substituents. Similarly, a group having 1-5 substituents refers to groups having 1, 2, 3, 4, or 5 substituents, and so forth.

Test Protocol—Feasibility Study Hand Blended Vs. Co-Precipitation

This test protocol outlines the procedures, analyses, results and conclusions comparing hand blended materials against blends made by the co-precipitation methods disclosed herein.

PURPOSE: This report provides the tests and data performed and captured in R & D notebooks regarding feasibility of co-precipitation (coppt) of PEG crosslinker blend studies and tests, with and without the colorant Indocyanine Green (IcG). All notebooks are in accordance with Neo-Mend Notebook OP05-04 Lab Notebook.

SCOPE: This report will compare initial and pertinent Adhesion Barrier, AB, product characteristics from a co-precipitated process used to create the AB PEG Blend including Indocyanine Green (coppt AB:IcG), to the previously hand blended preparation of the AB PEG crosslinker. These tests include burst, degradation and elastic modulus, G*.

OBJECTIVES: Previously, AB PEG blends were prepared in bulk by weight, and mixed by hand mechanical means; such as shaking or inversion rotation. FD&C Blue #2 was added to the AB PEG blend prior to shifting to the final formula where Indocyanine Green (IcG) was incorporated into the PEG Blend. Vials were filled by hand to a weighed mass, with no assurance of homogeneity between vial to vial, or lot-to-lot.

The data collected and presented here compares the results between the two PEG preparation methods in order to:

First, determine the significant difference on AB chemistry and properties, if any, due to preparing the PEG Blend by co-precipitation versus the hand blended method.

Second, to confirm that the addition of Indocyanine Green (IcG)

Neither interferes with the chemistry of the two AB components nor affects the AB product's properties.

Definitions

Coppt: Co-precipitated PEG=Co-precipitated PEG(SS)2+[PEG(SG)4-2LA]

Coppt IcG:AB=Co-precipitated PEG(SS)2+[PEG(SG)4-2LA]+Indocyanine Green

Hand Blended AB PEG=mixing the two PEG crosslinkers in bulk, either with a colorant additive (FD&C Blue #2 or Indocyanine Green) or not, then shaking the container by hand or inverting the container to attempt to create a homogenous mix.

NT=Not Tested
Control Time=Test point prior to ebeam
Zero Time=Test point after ebeam
IcG=Indocyanine Green
HSA=Human Serum Albumin
rHA=recombinant Human Albumin
Data and Analysis Hand Blending: No Color Versus with IcG.

Table 1 provides data from lots prepared by Neomend using the hand blending process for the AB Product, P-003. This data provides the baseline for the product and comparison to variations such as e-beam, color additive, or the co-precipitation process. All materials were made with recombinant human albumin purchased from Novozymes, and the data was from material which did not experience sterilization by ebeam. The results for the color free blended PEG was from two different test studies as noted in the Table 1.

TABLE 1

Hand Blended Pre ebeam AB Product

| Hand blended | Colorant | Burst (mmHg) | Std Dev (mmHg) | Degradation (Days) | G* (kPa) | std dev (kPa) |
|---|---|---|---|---|---|---|
| EWO-0019 | IcG | 226 | 30 | 10 | 56.7 | 8.1 |
| TR-0211 (PEG Dilactide) Burst and Degradation NB # 202,116 for G* | none | 236 | 12 | 10 | 54 | 8 |

The most simple AB PEG formula contains a blend of PEG(SG)4-2LA and PEG(SS)2-no color additive. The burst results indicate values >200 mmHg, and in-vitro hydrolysis occurring at 10 days. Since the burst and the degradation for EWO-0019 with IcG present were 226 mmHg and 10 days respectively. Addition of the IcG creates no significantly interference with, or affect on, these properties. The specifications for these two properties for the AB product are >90 mmHg and <30 days hydrolysis. All results in Table 1 meet these criteria. The elastic modulus is tested for information only. However, it will be used to help determine potential differences in the final hydrogel crosslink network of the two PEG preparation methods compared in this report, and of the various test conditions of the coppt methods.

Co-Precipitation: No Color Versus with IcG

Table 2 contains data for pre e-beam product prepared using coppt AB and coppt AB:IcG, prepared by Laysan Bio, for the AB project P-003. This table provides burst, degradation, and elastic modulus test results on 5 different co-precipitation processes for comparison to hand blend from Table 1 above. Samples 124-1 through 124-6 covers 5 different co-precipitation methods used by Laysan Bio utilizing various solvents and conditions. No color additive was incorporated. See above for descriptions and details of each trial. The data in the last two rows consists of two coppt runs where IcG was included to create the coppt AB:IcG crosslinker.

TABLE 2

Co-precipitated Pre ebeam AB Product

| Co-ppt Batches | Colorant | Burst (mmHg) | Std Dev (mmHg) | Degradation (Days) | G* (kPa) | std dev (kPa) |
|---|---|---|---|---|---|---|
| 124-1 | None | 234 | 31 | 10 | 56 | 7 |
| 124-2 | None | 224 | 30 | 10 | 54 | 12 |
| 124-4 | None | 235 | 42 | 10 | 55 | 14 |
| 124-5 | None | 234 | 6 | 10 | 48 | 8 |
| 124-6 | None | 204 | 33 | 10 | 64 | 15 |
| 124-54 | IcG | 202 | 50 | 11 | 67 | 11 |
| 124-50 (TR-0300) | IcG | 237 | 14 | 11 | 51 | 17 |

Table 2 shows that burst pressures results from the coppt AB PEG are all >200 mmHg, independent of the coppt method, or if the IcG colorant is present. All compare favorably to the burst results in Table 1 above and meet the AB product criteria of >90 mmHg The degradation results for all the coppt methods, including IcG, meet the criteria of hydrolyzing <30 days, and in fact agree well with the degradation results seen in Table 1.

The Elastic modulus, G*, for all the coppt methods tested in Table 2, again with or without IcG present, are comparable to the G* values listed in Table 1, 56.7 kPa for PEG with colorant, and 54 kPa for colorant free hand blended PEG. There is no significant difference in the crosslink network density due to any of the coppt methods, whether IcG is present or not, nor compared to the hand blended PEG in Table 1.

Ebeamed Product: Hand Blended Versus Co-Precipitated at 14.2 to 17.2 kGy

Table 3 provides data where the AB product was sterilized at an ebeam dose of 14.2 to 17.2 kGy. Burst, Degradation, and Elastic Modulus, G*, data are presented. The protein solution component consisted of material prepared using Novozme recombinant human albumin, except for the clinical batch Feb. 10, 2011. This batch was prepared with Human Serum Albumin, HSA, purchased from Baxter. The protein solutions were all pH 10.2 and buffered at 150 mM sodium carbonate.

Neomend prepared three of the four batches using the hand blending process; the fourth batch was prepared by Laysan Bio using the co-precipitation method. The first two rows contain hand blended PEG where the colorant FD&C Blue #2 was used. The third row provides e-beamed data from EWO-0019 where IcG replaced the FD&C Blue #2 in the hand blended PEG process, while row 4 contains the data from coppt AB:IcG Laysan Bio process.

TABLE 3

Post e-beamed AB Product, 14.2-17.2 kGy

| Lot/Reference | PEG Blend Method | Colorant | Burst (mmHg) | Std Dev (mmHg) | Degradation (Days) |
|---|---|---|---|---|---|
| Clinical 2/10/11:HSA | Hand | FD&C BLUE#2 | 233 | 10 | 13 |
| Clinical 8/10/11: rHA | Hand | FD&C BLUE#2 | 220 | | 12 |
| EWO-0019 | Hand | IcG | 260 | 22 | 10 |
| TR-0300 | Coppt | IcG | 200 | 48 | 11 |

The results for the AB properties after ebeam sterilization provided in Table 3 provide data for two comparisons. First, hand blended with FD&C Blue #2 to hand blended with IcG. Second, hand blended, with IcG or FD&C Blue #2, to coppt AB:IcG.

Hand Blended Comparison of Color Additives. There is no significant difference in properties between the hand blended PEG with IcG and the hand blended PEG with FD&C Blue #2.

The Burst results are >200 mmHg and successfully pass the criteria of >90 mmHg.

The degradation pass the criteria of <30 days for all cases and the difference between the 10 days for the IcG versus the 12 and 13 days for the FD&C Blue #2 is not significant, and is probably due to the variability of the hand blended technique, lot-to-lot preparation.

Hand Blended Versus Coppt AB:IcG. There was no significant difference in the AB Product properties due to the e-beam sterilization dose 14.2 to 17.2 kGy, independent of the PEG blending process, hand blended PEG compared to coppt AB:IcG PEG, and independent of the two color additives IcG and FD&C Blue #2.

Burst results of the coppt AB:IcG PEG are 200±48 mmHg and similar to all hand blended burst results. These results pass the >90 mmHg criteria and are similar to the hand blended PEG results.

At 11 days, the degradation for the coppt AB:IcG passes the <30 day requirement and falls between the hand blended degradation days of 10 to 13.

E-beam Versus Non e-beamed AB Properties Comparison of Hand Blended versus Coppt. The Coppt AB:IcG material properties after e-beam do not significantly differ from the hand blended AB PEG pre ebeam and is independent of the colorant used in the hand blended PEG.

Burst results of the Coppt AB:IcG was similar to the hand blended PEG at >200 mmHg, pre and post e-beam sterilization. All results successfully pass the criteria of >90 mmHg.

Degradation of the AB:IcG coppt PEG was similar to the hand blended PEG degradation, 10 to 13 days, pre and post e-beam sterilization. And, all results pass the criteria of <30 days.

The three primary tests used for comparison, burst, degradation and Elastic modulus, G*, show no significant difference between hand blending and coppt of the AB PEG crosslinker pre ebeam. While post ebeam the burst and degradation data show no significant difference between hand blending and coppt AB:IcG.

The data also shows that degradation, burst and Elastic modulus results are independent of the color additive IcG. There is no significant interference to the chemistry of the AB product or on the AB properties due to the presence of IcG.

The e-beam sterilization dose of 14.2 to 17.2 kGy on the AB product properties tested here, whether the PEG is prepared by hand blending technique or by co-precipitation, was minimal and not significant.

All Degradation data meet the criteria of <30 days.

All Burst results passed the Burst criteria of ≥90 mmHg.

The Elastic Modulus is for information only, but indicated in all cases a sufficiently crosslinked network for an adhesion barrier product.

The PEG AB product properties are consistent between all conditions tested. Consequently, the chemistry of the AB product and the resultant properties tested are not significantly affected due to any of the e-beam sterilization dose 14.2 to 17.2 kGy, the presence of FD&C Blue #2 or Indocyanine Green, the co-precipitation process compared to the hand blended process originally used to prepare the AB PEG component.

As noted, the co-precipitated product met all acceptance criteria wherein at time zero the products have an average burst test pressure must be >90 mmHg and Degradation of the AB product must be <30 days.

Thus, the tests conducted show that the co-precipitated products satisfy the product requirements, while benefitting from enhanced handling, consistency and other properties imparted by the co-precipitation method.

What is claimed is:

1. A method of preparing a homogenous multi-component PEG composition, the method comprising:
   providing a first solvent selected from the group consisting of methanol, 2-propanol, ethanol, methyl tert-butyl ether, dichloromethane, dimethyl sulfoxide (DMSO), and combinations thereof;
   providing at least a first component and a second component that are at least partially soluble in the first solvent;
   wherein the first component is a PEG functionalized with at least one electrophilic reactive group and/or nucleophilic reactive group, wherein the at least one electrophilic reactive group and/or nucleophilic reactive group is selected from one or more groups consisting of: butyraldehyde, propionaldehyde, epoxide, succinimidyl carbonate, nitrophenyl carbonate, succinimidyl carboxymethyl, succinimidyl glutarate, succinimidyl succinate, succinimidyl valerate, amines, amides, sulfhydryls, and thiols;
   contacting the PEG functionalized with the at least one electrophilic reactive group and/or nucleophilic reactive group, and the second component, together with the first solvent to at least partially dissolve the PEG functionalized with the at least one electrophilic reactive group and/or nucleophilic reactive group, and the second component, in the first solvent;
   wherein each of the PEG functionalized with the at least one electrophilic reactive group and/or nucleophilic reactive group, and the second component is co-precipitated by a process consisting of one or more co-precipitating steps selected from steps (a)-(c):
   a. reducing the temperature of the PEG functionalized with the at least one electrophilic reactive group and/or nucleophilic reactive group, and the second component, in the first solvent and maintaining the PEG functionalized with the at least one electrophilic reactive group and/or nucleophilic reactive group, and the second component, in the first solvent at a reduced temperature to form a co-precipitate of the PEG functionalized with the at least one electrophilic reactive group and/or nucleophilic reactive group, and the second component, in the first solvent, b. combining a second solvent with the PEG functionalized with the at least one electrophilic reactive group and/or nucleophilic reactive group, and the second component, in the first solvent and mixing for a period of time within a container to form a co-precipitate of the PEG functionalized with the at least one electrophilic reactive group and/or nucleophilic reactive group, and the second component, in a mixture of the first solvent and the second solvent, wherein the second solvent is selected from the group consisting of methanol, 2-propanol, ethanol, methyl tert-butyl ether, ethyl ether, dichloromethane, methanol, dimethyl sulfoxide (DMSO), acetonitrile, and combinations thereof, and/or c. subjecting the PEG functionalized with the at least one electrophilic reactive group and/or nucleophilic reactive group, and the second component, in the first solvent to a vacuum to form a co-precipitate of the PEG functionalized with the at least one electrophilic reactive group and/or nucleophilic reactive group, and the second component, by removal of the first solvent; and forming a substantially homogenous powder of the co-precipitate by drying the co-precipitate.

2. The method of claim 1, wherein the second component is selected from functionalized PEG, unfunctionalized PEG of similar MW, bioactive agents, antibiotics, statins, radiation sterilization stabilizers, peptide(s), therapeutic drug(s) or protein(s), nanoparticles, nanocages/nanoshells, colorants, disintegrates or dispersants, visual aids, therapeutic drugs and proteins, radiological markers, fibrins, thrombins, radiopacifiers, silver, antibiotics, chemo agents, growth factors, excipients, disintegrants and other molecular weight PEGs, or pegylated versions thereof.

3. The method of claim 1, wherein the first component and/or the second component is at least partially dissolved in a precursor solvent prior to the contacting step.

4. The method of claim 3, wherein the precursor solvent is independently selected from methanol, 2-propanol, ethanol, methyl tert-butyl ether, dichloromethane, dimethyl sulfoxide (DMSO), and combinations thereof.

5. The method of claim 3, wherein the precursor solvent is different from the first solvent and/or second solvent.

6. The method of claim 1, wherein the second component is a colorant.

7. The method of claim 6, wherein the colorant is indocyanine green (IcG).

8. The method of claim 1, wherein the second solvent has a different chemical composition than the first solvent.

9. The method of claim 1, wherein reducing the temperature of the PEG functionalized with the at least one electrophilic reactive group and/or nucleophilic reactive group and the second component in the first solvent comprises placing the PEG functionalized with the at least one electrophilic reactive group and/or nucleophilic reactive group and the second component in the first solvent in an ice bath.

10. The method of claim 1, wherein the co-precipitate is isolated by filtration.

11. The method of claim 1, wherein the PEG functionalized with the at least one electrophilic reactive group and/or nucleophilic reactive group comprises a cross-linking component.

12. The method of claim 1, wherein the first component is selected from the group consisting of: PEG di(succinimidyl succinimide) (PEG(SS)$_2$), PEG tetra(succinimidyl glutarate) (PEG(SG)$_4$), PEG tetra(succinimidyl glutarate)-di-lactide, and combinations thereof.

13. The method of claim 1, wherein the first component comprises a PEG functionalized with succinimidyl glutarate.

14. The method of claim 2, wherein the second component is a PEG functionalized with at least one electrophilic group and/or nucleophilic group, wherein the first component and the second component are different.

15. The method of claim 14, wherein the second component comprises a PEG functionalized with succinimidyl succinate.

16. The method of claim 1, wherein the first solvent comprises 2-propanol.

17. The method of claim 1, wherein the first solvent is a combination of ethanol and methyl tert-butyl ether.

18. The method of claim 1, wherein the first solvent is a combination of 2-propanol and DMSO.

19. The method of claim 18, wherein the first component comprises PEG(SS)$_2$.

20. The method of claim 19, wherein the second component comprises a colorant.

21. The method of claim 20, wherein the colorant comprises indocyanine green.

22. The method of claim 1, wherein the second solvent is ethyl ether or 2-propanol.

23. The method of claim 1, wherein the first solvent comprises dichloromethane and the second solvent comprises ethyl ether.

24. The method of claim 1, wherein the first solvent comprises dichloromethane and the second solvent comprises 2-propanol.

25. The method of claim 1, wherein forming the substantially homogenous powder of the co-precipitate by drying the co-precipitate comprises filtering the co-precipitate under argon gas and drying the co-precipitate under vacuum.

26. The method of claim 1, wherein the step of forming a substantially homogenous powder further comprises breaking up clumps of the homogeneous powder that form during drying.

* * * * *

UNITED STATES PATENT AND TRADEMARK OFFICE
CERTIFICATE OF CORRECTION

| | |
|---|---|
| PATENT NO. | : 11,571,493 B2 |
| APPLICATION NO. | : 14/384130 |
| DATED | : February 7, 2023 |
| INVENTOR(S) | : Tina Lanette McArthur et al. |

It is certified that error appears in the above-identified patent and that said Letters Patent is hereby corrected as shown below:

On the Title Page

In the Abstract, item (57), replace "the two or more components are at least and partially soluble in a solvent" with --the two or more components are at least partially soluble in a solvent--

In the Specification

At Column 10, Line 28, replace "4Arm-PEG-dl-SG MK" with --4Arm-PEG-dl-SG 10K--

At Column 16, Line 56, replace "Feb. 10, 2011" with --2/10/11--

Signed and Sealed this
Ninth Day of April, 2024

Katherine Kelly Vidal
*Director of the United States Patent and Trademark Office*